United States Patent [19]
Kelly

[11] Patent Number: 5,545,673
[45] Date of Patent: *Aug. 13, 1996

[54] METHOD FOR REDUCING RISK OF INFECTION BY SEXUALLY TRANSMITTED VIRUSES

[76] Inventor: Patrick D. Kelly, 33 Berry Oaks, St. Louis, Mo. 63122

[*] Notice: The term of this patent shall not extend beyond the expiration date of Pat. No. 5,482,053.

[21] Appl. No.: 368,041

[22] Filed: Jan. 3, 1995

Related U.S. Application Data

[60] Continuation-in-part of Ser. No. 57,110, May 3, 1993, abandoned, which is a division of Ser. No. 737,169, Jul. 29, 1991, Pat. No. 5,208,031, said Ser. No. 57,110, is a continuation-in-part of Ser. No. 737,169, which is a continuation-in-part of Ser. No. 528,495, May 25, 1990, abandoned, which is a continuation-in-part of Ser. No. 362,058, Jun. 6, 1989, abandoned.

[51] Int. Cl.$^6$ .......................... A61K 47/30; A61K 47/38; A61K 47/06; A01N 25/04
[52] U.S. Cl. .................... 514/772.3; 514/772.6; 514/774; 514/777; 514/781; 514/785; 514/786; 514/886; 514/931; 514/944; 514/966; 514/967; 514/968; 514/969; 424/401; 424/405
[58] Field of Search ...................... 424/401, 405, 424/407; 514/774, 777, 781, 785, 786, 886, 931, 944, 966, 967, 968, 969, 772.3, 772.6

[56] References Cited

U.S. PATENT DOCUMENTS

| | | | |
|---|---|---|---|
| 4,407,818 | 10/1983 | Lionelle et al. | 424/289 |
| 4,465,666 | 8/1984 | Lukas et al. | 424/145 |
| 4,548,950 | 10/1985 | Baxendale et al. | 514/510 |
| 4,604,404 | 8/1986 | Munson et al. | 514/494 |
| 4,869,270 | 9/1989 | Ueno et al. | 128/844 |
| 4,992,259 | 2/1991 | Schiraldi et al. | 424/49 |

FOREIGN PATENT DOCUMENTS

87/02246  10/1987  WIPO.

OTHER PUBLICATIONS

Brawner, T. A., et al, *Arch. Dermatol. Res.* 265:71–77 (1979).
Brody, I., *Brit. J. Dermatol.* 104:191–194 (1981).
Eby, G. A., and W. W. Halcomb, *Medical Hypotheses* 17:157–165 (1985).
Fahim, M., et al, *J. Medicine* 9:245–264 (1978).
Fahim, M., et al, *J. Medicine* 11:143–167 (1980).
Fahim, M. S. and Brawner, T. A., *Arch. Andrology* 4:79–85 (1980).
Tennican, P. O., et al, *Life Sciences* 24:1877–1884 (1979).
Tennican, P., et al, *Proc. Soc. Exp. Biol. Med.* 164:593–597 (1980).

(List continued on next page.)

*Primary Examiner*—Carlos Azpuru
*Attorney, Agent, or Firm*—Patrick D. Kelly

[57] ABSTRACT

A method is disclosed for reducing the risk of infection by sexually transmitted viruses. This method involves spreading a lubricant fluid containing a selected zinc salt across the surfaces of the penis or vagina, before intercourse, in a manner that causes the lubricant to coat and remain in contact with the genital surfaces throughout intercourse. The zinc salt should be organic, water-soluble, non-irritating, physiologically acceptable, and have a high rate of dissociation, which allows it to release substantial quantities of divalent zinc ions. Suitable zinc salts include zinc acetate, zinc propionate, zinc butyrate, zinc formate, zinc gluconate, zinc glycerate, zinc glycolate, and zinc lactate. A preferred carrier fluid comprises a lubricant gel, which also contains water, a thickening agent (such as chemically treated cellulose) and a lubricating agent (such as glycerin). The lubricant formulation must be free of heparin, dextran sulfate, or any other component that poses a substantial risk of adverse effects if the lubricant is used frequently and repeatedly over a period of months or years. The lubricants disclosed herein preferably should be used with condoms, to enhance the risk-reducing effectiveness of condoms and provide maximum protection; however, these lubricants can also be used without condoms, if desired.

7 Claims, 2 Drawing Sheets

OTHER PUBLICATIONS

Wahba, A., *Acta Derm. Vernerol.* (Stockholm) 60:175–177 (1980).

Fitzherbert, J. C., *Med. J. Australia,* May 5, 1979, p. 399.

Fridlender, B., et al, *Virology* 84:551–554 (1978).

Gordon, Y. J., et al, *Antimicrob. Agents Chemother* 8:377–380 (1975).

Gupta, P., and Rapp, F., *Proc. Soc. Exp. Biol Med.* 152:455–458 (1979).

Jones, R., *Med. J. Australia,* Apr. 7, 1979, p. 286.

Shlomai, J., et al, *Virology* 66:330–335 (1975).

Sergio, W., *Medical Hypotheses* 26:251–253 (1988).

Cannan, R. K., and Kibrick, A., *J. Amer. Chem. Soc.* 60:2314–2320 (1938).

Williams, W. L., *Contraception* 6:659–672 (1980).

Merck Index, 1989, pp. 1598–1601.

METHOD FOR REDUCING RISK OF INFECTION BY SEXUALLY TRANSMITTED VIRUSES

RELATED APPLICATIONS

This is a continuation-in-part of U.S. application Ser. No. 08/057,110, filed on May 3, 1993, now abandoned, which was a divisional and continuation-in-part of U.S. application Ser. No. 07/737,169, filed on July 29, 1991, which issued as U.S. Pat. No. 5,208,031 on May 4, 1993. That application was a continuation-in-part of application Ser. No. 07/528,495, filed on May 25, 1990, now abandoned, which was a continuation-in-part of application Ser. No. 07/362,058, filed on Jun. 6, 1989, also abandoned.

BACKGROUND OF THE INVENTION

This invention is in the fields of biochemistry, pharmacology, and anti-viral agents.

There is a major need for methods to prevent the spread of viruses that are transmitted through sexual contact, including genital herpes viruses (herpes simplex virus type 2, HSV-2), the human immunodeficiency virus (HIV, the causative agent of AIDS), hepatitis viruses, and papilloma viruses. Extensive information on each of these viruses is contained in numerous medical books and articles; for example, Mindel 1989 offers a good overview of herpes viruses, while the October 1988 issue of *Scientific American* offers a good overview of HIV and AIDS.

Once contracted, herpes and HIV are incurable, since the viruses insert their DNA into the chromosomes of infected cells. The fact that these viruses are incurable highlights the need for methods to reduce the rates and incidence of infection among people who are not yet infected. The subject invention is directed solely toward that goal. This invention is not a treatment for people who are already infected with herpes, HIV, or any other sexually transmitted virus; instead, it is a method of reducing the risk of infection among people who are not infected, but who may be exposed to sexually transmissible viruses through intercourse with potentially infected sexual partners. Briefly, this invention involves topical lubricants that are spread on the surfaces of the genitals before and during sexual intercourse, which contain a selected zinc salt as an anti-viral agent. The lubricant must be non-irritating, physiologically acceptable, and free of any adverse long-term effects when used frequently over a prolonged period of time. Preferred zinc salts include relatively low molecular weight organic salts which have high solubility in water, and which have low pK values (which indicates high levels of ionic dissociation to release free divalent zinc ions, $Zn^{++}$). Such salts include zinc acetate and zinc propionate. Other organic salts that have somewhat lower levels of solubility or dissociation, but which can be used if desired, include zinc butyrate, formate, gluconate, glycerate, glycolate, and lactate. All of these organic salts which have been tested to date have not caused any irritation in skin, genital, or intercourse tests. By contrast, zinc sulfate (which has been used in the past by numerous other researchers trying to find effective ways to treat herpes infections) causes significant levels of irritation in most people, and is not preferred. Although substantial irritation will be tolerated by people who are already infected by genital herpes and who are suffering an outbreak of lesions, such levels of irritation are not acceptable in a genital lubricant intended for use during sexual intercourse.

Prior Studies on Zinc Salts To Treat Genital Herpes

Prior to this invention, numerous researchers reported that zinc could inhibit herpes viruses. Some of these test reports involved in vitro cell culture tests (e.g., Gordon et al 1975, Shlomai et al 1975, Gupta and Rapp 1976, Fridlender et al 1978, and U.S. Pat. No. 4,407,818 by Lionelle et al). Other test reports involved in vivo tests on people or lab animals that had already become infected with herpes viruses (e.g., DeRoeth et al 1963, Jones 1979, Tennican et al 1979 and 1980, Fahim et al 1980a and 1980b, Wahba et al 1980, Brody et al 1981, Eby and Halcomb 1985, and U.S. Pat. Nos. 4,465,666 and 4,762,715 (Lukas et al)).

Most of that work was done before the advent of nucleoside analogs such as acyclovir and gancyclovir. Interest in zinc as a topical anti-herpetic treatment dropped off sharply after "high-tech" drugs such as acyclovir offered more effective treatments.

It should also be noted that several of the articles cited above report that zinc salts, by themselves, are not effective in inhibiting herpes viruses unless they are combined with some other agent or treatment that increases the effectiveness of the mixture. For example, the reports by Fahim et al involve ultrasound treatment of areas treated by ointments containing 30% urea, 3% zinc sulfate, and 2% tannic acid. Obviously, ultrasound treatment of the site of transmission during sexual intercourse is not feasible.

Similarly, U.S. Pat. No. 4,465,666 (Lukas et al) stated that zinc salts by themselves were not adequately active against herpes viruses. In order to render the zinc salts effective for treating herpes, Lukas '666 stated that a sulfated polysaccharide such as heparin or dextran sulfate had to be added to the mixture. However, it would be inadvisable to add heparin or dextran sulfate to a genital lubricant, since repeated use of either agent in a genital lubricant could generate severe adverse effects. Heparin is a powerful anti-coagulant, and it inhibits the growth of epithelial cells, which are the type of cells that line the mucous membranes inside the vagina and urethra (Wright et al 1985 and 1987). Both of these traits indicate that heparin is likely to interfere with the closure and healing of any lesions, cuts, and microabrasions in the mucous membranes or other genital surfaces. Heparin administration has also been associated with skin necrosis (White et al 1979), and heparin apparently is able to penetrate the skin and enter the bloodstream (Aliabeva et al 1980). All of these factors indicate that heparin would generate various risks of adverse effects in a substantial portion of the general population.

Dextran sulfate appears to be even more dangerous. It causes severe ulcerations and inflammation in the colon, and can lead to colon cancer; this effect is so strong that dextran sulfate is used as the causative agent in a standard laboratory technique which induces ulcerative colitis and colon cancer in lab animals (e.g., Cooper et al 1993 and Yamada et al 1992). It also interferes with fibroblast growth, various types of fluid and cell movement and permeation, and other natural processes involving the skin (see Sorimachi et al 1992, Van Osselaer et al 1993, and Powis et al 1992). In addition, dextran sulfate is also an anti-coagulant. Although less powerful than heparin, it can interfere with the healing and closure of lesions or small cuts or abrasions in the skin or mucous membranes of the genitals.

These adverse effects are regrettable, since both heparin and dextran sulfate have been shown to have substantial activity in cell culture tests against HIV, the virus that causes AIDS. However, these risks and adverse effects cannot be ignored, and they apparently render heparin and dextran sulfate dangerous and unsuitable for use in genital lubricants. U.S. Pat. No. 4,869,270 (Ueno et al 1989), which claimed the use of dextran sulfate in a condom lubricant, made no mention of the problem of ulcerative colitis caused by dextran sulfate, or any of the other physiological problems and dangers listed above.

It should also be noted that most of the above-cited reports involving herpes viruses used zinc sulfate, which causes genital irritation and is therefore not well suited to use as a lubricant during intercourse.

Studies on Zinc Which Failed to Show Inhibition of HIV

A number of researchers have performed screening studies on various zinc compounds, to determine whether such compounds might be able to inhibit HIV, the virus that causes AIDS. However, none of the published studies that used standardized assays showed any effectiveness for zinc as an anti-HIV agent. Very little has been published in scientific or medical journals regarding such tests, since the results were poor; however, the lack of success using zinc against HIV can be documented using items of personal correspondence.

For example, when the Applicant submitted samples of several zinc salts (including zinc acetate and zinc gluconate) to the National Cancer Institute for evaluation in a standardized screening test used to evaluate drugs against HIV (described in Weislow et al 1989), the scientists in charge of the NCI's screening program returned the zinc salts without even opening them. The NCI's letter of response addressed to the Applicant, dated Aug. 8, 1991, stated as follows: "After careful consideration, we have decided not to test your zinc salts in our AIDS-antiviral assay . . . We have tested 36 zinc-containing compounds in our in vitro AIDS screen, including zinc gluconate. Test results of this inactive compound, NSC 619899, are enclosed . . . None of these materials has demonstrated any activity worth pursuing . . . Based on these results, we don't believe that your compounds will show activity in our assay."

This is an authoritative statement by researchers skilled in the art of HIV research who had tested zinc against HIV, and who did not believe that zinc salts could serve as effective agents against HIV infection.

The Applicant has also been informed by an official of Contraceptive Research and Development (CONRAD, a not-for-profit foundation based in Alexandria, Va.) that several zinc salts were tested using an assay described in Resnick et al 1990. According to the CONRAD official, the results of those tests did not show any substantial anti-HIV activity for any zinc compounds.

Other Prior Art

Another line of prior art also deserves mention, even though it does not involve anti-viral research. In the late 1970's, several zinc salts were studied to determine whether they might be effective as contraceptives to avoid pregnancy (Williams 1980, Chvapil 1978, and Chvapil 1980). Williams 1980 tested several formulations, including zinc acetate mixed with K-Y Lubricating Jelly (a trademark for an aqueous gel sold by Johnson & Johnson, New Brunswick, N.J.). The zinc salts tested by Williams and Chvapil were only about 80% effective on a single-event basis. This is not nearly good enough for practical and effective use as a contraceptive; to be effective as a contraceptive at a 95% or higher level over the span of a year or more (where a failure in any single act of intercourse, out of numerous acts of intercourse during the year, results in pregnancy), a contraceptive must be effective at well over the 99% level during each act of intercourse. Since the results reported by Williams and Chvapil showed that zinc salts did not have adequate contraceptive activity, there were no subsequent reports involving zinc as a contraceptive, and interest in this line of research apparently died out.

Accordingly, there remains a need for a non-irritating, non-toxic genital lubricant for use during sexual intercourse, to reduce the risk of viral infection in someone who is not previously infected. Any such lubricant must be safe and harmless enough for frequent and repeated use (such as daily use) over a period of months or years. Terms such as frequent, repeated, or daily use do not imply that the same quantity of lubricant will be used repeatedly; instead, a new quantity of the lubricant will be used during each act of intercourse. To be suitable for such use, a lubricant must be free of any component which is an anti-coagulant (such as heparin or dextran sulfate) or which could pose a risk of adverse effects if used frequently and repeatedly over a span of months or years.

One object of this invention is to disclose a method of using an aqueous gel containing a non-irritating, non-toxic zinc salt as a topical genital lubricant during sexual intercourse, with or without a condom, to reduce the risk of viral infection in someone who is not previously infected with a sexually transmitted virus such as genital herpes.

SUMMARY OF THE INVENTION

A method is disclosed for reducing the risk of infection by sexually transmitted viruses. This method involves spreading a lubricant fluid containing a selected zinc salt across the surfaces of the penis or vagina, before intercourse, in a manner that causes the lubricant to coat and remain in contact with the genital surfaces throughout intercourse. The zinc salt should be organic, water-soluble, non-irritating, physiologically acceptable, and have a high rate of dissociation, which allows it to release substantial quantities of divalent zinc ions. Suitable zinc salts include zinc acetate, zinc propionate, zinc butyrate, zinc formate, zinc gluconate, zinc glycerate, zinc glycolate, and zinc lactate. A preferred carrier fluid comprises a lubricant gel, which also contains water, a thickening agent (such as chemically treated cellulose) and a lubricating agent (such as glycerin). The lubricant formulation must be free of heparin, dextran sulfate, or any other component that poses a substantial risk of adverse effects if the lubricant is used frequently and repeatedly over a period of months or years. The lubricants disclosed herein preferably should be used with condoms, to enhance the risk-reducing effectiveness of condoms and provide maximum protection; however, these lubricants can also be used without condoms, if desired.

DESCRIPTION OF THE PREFERRED EMBODIMENTS

This invention relates to a method of using certain types of zinc salts in genital lubricants during sexual intercourse.

Such lubricants can be used by someone who is not infected with a sexually transmitted virus such as herpes or HIV, and who is concerned about the risk of infection from a sexual partner who may be infected. One method of applying a lubricant gel to the genitals involves removing a small quantity of gel (such as a teaspoon, or several milliliters) from a container such as a plastic or metallic tube or a sealed plastic packet, and spreading the gel across the surface of the penis immediately before intercourse. Alternate methods of emplacement include (1) spreading the gel upon accessible surfaces inside the vagina shortly before intercourse, or (2) emplacing a condom that has already been coated with a zinc-containing lubricant upon the penis or inside the vagina.

Any of these methods of spreading a zinc-containing lubricant across the surfaces of the genitals should cause the lubricant to coat and remain in contact with the genital surfaces throughout intercourse. During and after intercourse, the zinc salt dissolved in the lubricant will act as an antiviral agent, like a chemical barrier at the site of transmission, to reduce the risk that a previously uninfected user will become infected by a sexually transmitted virus if a sexual partner is infected.

Such lubricants preferably should be used in conjunction with condoms, to enhance the risk-reducing effectiveness of condoms and provide maximum protection for users. Such an increase in the anti-viral protection offered by a condom can become important if a condom breaks, or if the male loses his erection prior to withdrawal and there is spillage or leakage of fluid from inside the condom into the vagina. The lubricant fluid can either be coated onto condoms during manufacture and enclosed within conventional watertight plastic or foil packages that contain one condom per package, or it can be manually applied by a user to either the inside or the outside of a condom immediately before use.

As used herein, "condom" refers to a barrier device which is used to provide a watertight physical barrier between male and female genitalia during sexual intercourse, and which is removed after intercourse. This term includes conventional condoms which cover the penis; it also includes so-called "female condoms" which are inserted into the vaginal cavity prior to intercourse. The term "condom" does not include diaphragms, cervical caps, or other barrier devices which cover only a portion of the epithelial membranes inside the vaginal cavity. Preferably, condoms should be made of latex, which provides a higher degree of protection against viruses than so-called "lambskin" or "natural membrane" condoms.

Although aqueous gel formulations (described in more detail below) are preferred for "stand-alone" lubricants that are not packaged with condoms, zinc-containing lubricants that are packaged with condoms do not require gels. A lubricant packaged with a condom requires only a water-soluble lubricating agent, such as glycerin or propylene glycol, along with a suitable zinc salt. Other components, such as water and a thickening agent, may be added to a condom lubricant if desired.

As used herein, terms such as "genital lubricant" and "topical use" refer to something that is applied to and spread across the surface of the skin or a mucous membrane. A condom lubricant or other genital lubricant used as described herein is a topical agent, even though it enters the cavity or vault of the vagina, since it does not permeate through the skin or mucous membrane and enter the bloodstream in significant quantities. By contrast, "systemic" administration refers to drugs that are ingested orally or injected beneath the skin.

Although the efficacy and practical use of this invention do not depend on a specific molecular mechanism, it appears that the mechanism by which zinc inactivates herpes viruses and HIV may involve the formation of crosslinking bonds. Positively charged divalent zinc ions ($Zn^{++}$) bind to negatively charged unshared electron pairs on the residues of certain types of amino acids (mainly cysteine and histidine) in proteins. This type of crosslinking reaction is extremely important to certain types of enzymes; in particular, it creates and stabilizes the "finger domains" in zinc finger proteins, which carry out crucial interactions with chromosomal DNA in the nucleus of every living cell on earth.

In the topical lubricant formulations described herein, a similar type of protein crosslinking reaction apparently allows free zinc ions to react with proteins on the surfaces of mammalian viruses. This causes virus particles to agglomerate and bind randomly to each other, and to the surfaces of various cells that cannot be infected, including epidermal and epithelial cells on the skin and mucous membrane surfaces of the penis and vagina. These more-or-less random binding reactions reduce the ability of the crosslinked viruses to contact and infect cells that would be susceptible to active infection by the viruses.

This crosslinking reaction has not been reported in any of the scientific and medical reports that describe the use of zinc salts to inhibit viruses. The prior art has reported numerous putative mechanisms which appear to contribute to the antiviral activity of zinc salts, including interference with post-translational processing of capsid polypeptides in rhinoviruses (Korant and Butterworth 1976), inhibition of DNA polymerase in herpes viruses (Shlomai et al 1975; Fridlender et al 1978), interference with herpes protein synthesis (Gupta and Rapp 1976), inhibition of thymidine kinase accumulation and a possible alteration of RNA synthesis in vaccinia viruses (Zaslavsky 1979), and interference with procapsid synthesis in foot-and-mouth disease viruses (Firpo and Palma 1979). All of these reported mechanisms appear to be consistent with the ability of zinc to form crosslinking bonds with proteins, and the crosslinking mechanism suggested herein may offer a unifying explanation for the numerous other molecular mechanisms that have been reported in the prior art.

Absence of Irritation by Zinc Acetate in a Gel Carrier

One of the crucial discoveries that led to the subject invention was the discovery, by the Applicant, that certain types of zinc salts can be included at substantial concentrations in gels which can be used as genital lubricants during a complete act of intercourse, without causing any noticeable irritation to either the male or female. This discovery was significant and unexpected, for three reasons.

First, much of the prior research which used zinc salts against herpes viruses used zinc sulfate, which causes substantial burning and irritation in most people, especially on mucous membranes. Burning and irritation can be tolerated in a treatment for herpes lesions, if the treatment will make the lesions heal more rapidly in someone who is already infected. However, significant burning and irritation will not be tolerated by most people in genital lubricants intended for use during intercourse.

Second, the absence of any irritation by salts such as zinc acetate and zinc propionate when dissolved in a gel is somewhat surprising, since zinc acetate and zinc propionate each cause a substantial amount of burning and irritation when dissolved in water alone. This unexpected disappearance of any irritation when zinc acetate is dissolved in a gel carrier, rather than water, is described in more detail below.

And third, zinc salts are well known to be astringents (agents that cause a drying effect, blood vessel constriction, and/or tissue contraction). The Merck Index (11th edition, 1989) explicitly lists nearly all the zinc salts that are of pharmaceutical interest (including zinc acetate, zinc carbonate, zinc chloride, zinc iodide, zinc salicylate, zinc stearate, zinc sulfate, and zinc tannate) as astringents. Astringents are well-suited for treating outbreaks of herpes, since one of the main goals of treating herpes lesions is to dry out the virus-laden fluid that fills the blisters and lesions. However, an astringent is the opposite of what people normally want in a lubricant, especially a lubricant applied to the genitals during intercourse. People do not want drying, vasoconstricting, or other astringent actions at their genitals during intercourse. Therefore, the fact that zinc salts are astringents teaches away from their use in condom lubricants. However, in this invention, the use by the Applicant of a suitable lubricant gel carrier substance made primarily of water, and which contained thickening and lubricating agents in addition to the water, overcame the astringent effects of zinc. No unpleasant or noticeably astringent effects were observed by the people who tested gels with zinc acetate or zinc propionate in gels during intercourse.

Suitable Zinc Salts

As mentioned above, the anti-viral activity of a zinc salt in an aqueous carrier is presumed to be due to the action of free divalent zinc ions that have been released by the salt. Three factors are important in determining the concentration of zinc ions that will be present in an aqueous carrier fluid if a certain zinc salt is dissolved in the fluid. Those factors are:

(1) The solubility of the zinc salt in water. This value is often expressed in terms of grams of salt per 100 cubic centimeters (0.1 liter) of saturated solution. That figure can be converted into a grams/liter basis by multiplying it by 10.

(2) The molecular weight of the salt, which allows a weight concentration to be converted into a molar concentration. For example, the molecular weight of zinc acetate is 183.4, so 183.4 grams of zinc acetate is equal to one mole ($=6.02\times 10^{23}$ molecules). Molar concentrations are usually expressed in molar (M) units, which refer to moles of a compound per liter of solution, or in millimolar (mM) concentrations, which refer to thousandths of a mole per liter.

(3) The rate at which the salt dissociates into cations and anions. This is usually expressed on a base 10 logarithmic scale using pK values, which are often called equilibrium constants, stability constants, or dissociation constants. Like pH values for acids, if the pK value of a salt is low, the rate of ionic dissociation for that particular salt is high.

Solubility and pK values for several zinc salts are provided in Table 1. These values were obtained from published reports (Sillen and Martell 1964 and 1971, Lide 1990, Linke 1965, and Cannan and Kibrick 1938). From a review of several articles cited by Sillen and Martell, it appears that (1) reported pK values of less than 2 refer to the release of a single carboxy anion from a zinc salt, and (2) reported pK values of more than 2 (e.g., Griessar et al 1968) refer to the release of divalent zinc ions by dissociation of two carboxy anions. There are several methods for measuring ion concentrations, and variations in values between different published papers reflect differences in the method of measurement.

Since zinc gluconate has already been reported to be effective in combatting established herpes infections (Eby and Halcomb 1985), zinc gluconate can be regarded as a benchmark of effectiveness. Other zinc salts that are comparably soluble (or preferably more soluble) and which have comparable (or preferably lower) pK values, when compared to zinc gluconate, can be presumed to be effective in inhibiting herpes virus. The anti-viral effectiveness of any such zinc salt in aqueous solution, or in a complete lubricant formulation, can be tested using in vitro tissue culture tests or in vivo animal tests as described in above-cited U.S. Pat. No. 5,208,031 (the teachings of that patent are hereby incorporated by reference).

All of the organic zinc salts listed in Table 1 are good candidates for use in anti-viral lubricants as described herein. Two salts which are especially preferred, because they have high solubility in water and high ionic dissociation rates (low pK values), are zinc acetate and zinc propionate.

Among other things, this invention is based on the discovery that certain zinc salts that are soluble in water do not irritate the skin or mucosal membranes of the penis or vagina, even when a lubricant containing such a salt is rubbed into the skin or membrane over a sustained period of time, as occurs during intercourse. Zinc acetate and zinc propionate were both tested for irritation; although each of them caused vaginal irritation when dissolved in water alone, they were found to be non-irritating when mixed with K-Y Lubricating Jelly at concentrations up to about 5% weight/volume and used as a lubricant during a complete act of heterosexual intercourse.

TABLE 1

PROPERTIES OF VARIOUS ORGANIC SALTS OF ZINC

| Salt | Solubility (grams/liter) | Molecular weight | Molar solubility (moles/liter) | Reported pK values |
|---|---|---|---|---|
| Zinc acetate | 300 (25° C.) | 183.4 | 1.64 | 1.03 |
| Zinc propionate | 320 (15° C.) | 211.5 | 1.51 | 1.01 |
| Zinc butyrate | 107 | 275.6 | 0.4 | 1.00 |
| Zinc formate | 52 (20° C.) | 155.4 | 0.33 | $pK_1 = 0.6, pK_2 = 0.95$ |
| Zinc gluconate | 127 (25° C.) | 455.7 | 0.28 | 1.70 |
| Zinc glycerate (dihydroxypropionate) | NA | 275.6 | NA | 1.80 |
| Zinc glycolate (hydroxyacetate) | NA | 215.5 | NA | 1.92 |
| Zinc lactate | 57 | 279.5 | 0.20 | 1.86 |

Sources:
Sillen and Martell 1964 and 1971
Lide 1990
Linke 1965
Cannan and Kibrick 1938

Zinc butyrate also has a high rate of ionic dissociation; since it is less soluble than zinc acetate or propionate, it was not tested for irritation.

Zinc gluconate was also tested and did not cause any irritation during intercourse. However, it does not have a high degree of solubility in water, and when extensively ground in a mortar and pestle and then mixed thoroughly in a gel, the gel contained very fine, small particles which displayed a very slight roughness when rubbed hard between the forefinger and thumb. Although no abrasion or irritation was noticeable by either personduring intercourse, it is not recommended for use in a lubricant, due to the risk of creating microabrasions that might help viral particles penetrate skin or mucous membranes.

Other organic salts that appear to be less preferred, since they are less soluble in aqueous solution and/or because they have relatively high pK values, include zinc salicylate, zinc citrate, zinc oleate, zinc benzoate, zinc laurate, and zinc tartrate. Several other organic salts of zinc were obtained and evaluated, including zinc stearate, zinc salicylate, and zinc valerate. None of those salts caused any irritation during forearm or male genital tests; however, each had other drawbacks. Zinc valerate, although soluble in water, has an unappealing dirty-looking color and an unpleasant odor. Zinc stearate and zinc salicylate have very low solubility in water, and also have unpleasant odors. Accordingly, even though they caused no irritation in forearm or male genital tests, they were not tested vaginally or during intercourse.

Although non-polymeric salts with low molecular weights are preferred, it may be possible to use a zinc salt formed from a polymeric component of a gel, such as a cellulose derivative or some other polymer or polysaccharide used as a thickening or lubricating agent. Several such polymeric compounds which might be converted into polymeric zinc salts for use herein are described below.

Zinc Salt Concentrations

Rather than trying to determine a single concentration of a zinc salt that would be optimal for everyone, the effectiveness of this invention can be enhanced by selling lubricants having a range of different zinc concentrations for different people. By way of analogy, since some people are easily sunburned while others are highly tolerant of direct sunlight, suntan oils and creams are sold with a range of "sun protection factors." Anyone is free to choose his or her preferred formulation, based on both skin type and anticipated exposure. As another example, contraceptive gels containing 1% to 4% nonoxynol, and condoms lubricated with fluids containing 5 to 15% nonoxynol, are both sold over-the-counter, and purchasers are free to choose the concentration they prefer.

In a comparable manner, genital lubricants having a range of concentrations of anti-viral zinc salts can be made available, and people having varying sensitivities, sexual habits, and levels of concern over sexually transmitted viruses, can choose the concentrations they prefer. People who are at relatively low risk, or who have sensitive skin or are highly susceptible to psychosomatic suggestions of irritation, might prefer to use a formulation having a relatively low concentration, such as about 0.5% to 3% expressed as weight per volume (w/v, calculated as grams of zinc salt per milliliter of fluid, multiplied by 100 to convert the ratio to a percentage). People who are highly sexually active and non-monogamous, or who live in cities with high rates of sexually transmitted diseases, might choose to use a lubricant containing 30% or more of a zinc salt. This 30% figure might seem high, but it should be noted that:

(1) It indicates the weight of the salt, rather than the weight of elemental zinc. A compound containing 30% w/v zinc acetate would contain about 10.7% elemental zinc.

(2) Preparations used for other surface applications are sold over-the-counter which contain more than 30% elemental zinc.

(3) Relatively small quantities of lubricant are typically used in conjunction with condoms. For example, while spermicidal gels for use without condoms usually contain about 5% or less nonoxynol as a spermicide, condom lubricants contain up to 15% nonoxynol. Accordingly, a gel intended for use with a condom may have a somewhat higher concentration of a zinc salt than a gel intended for use without a condom.

(4) The lubricant usually becomes diluted by the female's natural fluids after intercourse begins.

Accordingly, this invention anticipates genital lubricants containing zinc salts in the range of about 0.5% to about 30% w/v.

As used herein, references to "non-irritating" refer to formulations that cause no irritation, or acceptably low levels of irritation, in at least some people. Such formulations can be used by such people regardless of whether they might cause irritation in other people who are more susceptible. In addition, the anti-viral lubricants of this invention can be used even though they may cause some irritation in the user; many people would regard a low level of mild irritation as a reasonable and necessary price for an added level of safety, comparable to the loss of sensitivity that accompanies condom use.

Anyone buying such a lubricant should be clearly warned that the lubricant does not offer completely reliable, 100% protection against herpes infection. Nevertheless, the anti-viral sexual lubricants of this invention can reduce the risk of becoming infected. Accordingly, in the absence of any effective vaccines or cures for herpes or AIDS, most rational people who are at risk would prefer to take the precaution of using a lubricant which offers nearly any significant increase in protection, provided the lubricant is genuinely safe, non-toxic, and non-irritating.

Aqueous Gels (Carrier Fluids)

In addition to an anti-virally effective zinc salt, the gel carrier fluid of a lubricant as described herein should have the following components, which are discussed in more detail in the above-cited U.S. Pat. No. 5,208,031:

a. water;

b. a thickening agent such as cellulose or a chemically treated derivative of cellulose, acacia, agar, alginate, carrageenan, gum tragacanth, xanthan gum, collagen, carboxypolymethylene, glyceryl monostearate, polyvinylpyrrolidone, and polyacrylamide; and, c. a lubricating agent such as glycerin, propylene glycol, polyethylene glycol, polypropylene glycol, polyisobutene, polyoxyethylene, behenic acid, behenyl alcohol, sorbitol, and polydimethylsiloxane.

The thickening and lubricating agents listed above are not biologically active, and basically serve as carrier substances.

As used herein, "lubricating agent" refers to a component which is incorporated into a genital lubricant for the purpose of reducing friction during intercourse. Although any liquid (including water) can sometimes function as a "lubricant" in the broadest sense of the word, four characteristics distinguish a "lubricating agent," as that term is used herein, from water and other liquids that do not have the characteristics necessary for effective and comfortable lubrication during sexual intercourse: (1) a proper lubricating agent is substantially more viscous than water and feels slippery when rubbed between two skin surfaces; (2) a lubricating agent should have an affinity for human skin, and when applied to skin, it should spread smoothly and evenly across the contacted area; (3) a lubricating agent should remain in contact with the skin, clinging to it in a more substantial manner than water, which is easily wiped away; and, (4) a lubricating agent should have a low level of volatility, and should not evaporate quickly. The foregoing characteristics can be easily recognized and understood on a practical level by rubbing a conventional lubricating agent (such as glycerin or mineral oil) between the fingers. The nature and the durability of the lubrication, and the differences between such agents and less suitable liquids such as water, are readily apparent.

In addition, in order to be physiologically acceptable, a selected lubricating agent should not cause any significant adverse effects (such as irritation, tenderness, swelling, redness, or skin discoloration), and must not pose a significant risk as a carcinogen or teratogen. Further, in contrast to non-physiological lubricants such as motor oil, physiologically acceptable lubricating agents should be either gradually broken down into innocuous substances in the body if they are absorbed by tissue to a significant degree through the skin or mucous membranes, or they should be of a nature that allows them to be secreted by the vagina and washed cleanly from the skin, so that they will not foul and clog the pores in membranes or dermal layers.

Several lubricating agents which are used in commercially available sexual lubricants satisfy these criteria, including glycerin (also called glycerine, glycerol, 1,2,3-propanetriol, and trihydroxypropane) and certain types of polyethylene glycol (PEG), such as PEG 200 or PEG 400 (the numbers indicate different molecular weight averages). Various other polymers (such as polypropylene glycol, polyisobutene, and polyoxyethylene) and behenic acid and behenyl alcohol are also used as lubricants in cosmetics and other formulations that contact the skin. In addition, some sugar-alcohols such as sorbitol, and some silicon compounds such as polydimethylsiloxane, are also used as skin-contacting lubricating agents.

Because glycerin, propylene glycol, polyethylene glycol, and polypropylene glycol have long been used in sexual lubricants and other skin-contacting formulations with no adverse effects, they are preferred for use as lubricating agents in the anti-viral sexual lubricants of this invention. The suitability of any other candidate lubricating agent as a condom lubricant as described herein can be determined through routine experimentation in humans to ensure that it will not cause irritation or other adverse effects, and in in vitro cell culture and in vivo lab animal tests (as described in U.S. Pat. No. 5,208,031) to ensure that the candidate lubricating agent does not substantially reduce the anti-viral effectiveness of a lubricant gel containing a zinc salt.

Suitable thickening agents which are widely used in genital or other gels applied to the skin comprise chemically treated derivatives of cellulose (such as hydroxyethyl- or hydroxymethyl-cellulose). Other thickening agents which have been used in skin-contacting compounds, and which offer candidate agents for potential use in zinc-containing genital lubricants, include acacia, agar, alginate, carrageenan, gum tragacanth, xanthan gum, collagen, carboxypolymethylene, glyceryl monostearate, polyvinylpyrrolidone, and polyacrylamide.

Other components, including preservatives (such as chlorhexidine gluconate), anti-crystallization agents (such as glucono-delta-lactate), fragrances, coloring agents, alkaline or acidic or buffering agents to maintain the proper pH, and soothing or anti-swelling agents (such as lanolin, aloe vera extract, or hydrocortisone) can be added to the condom lubricants described herein. However, at the concentrations used, any such additive should not seriously impede the anti-viral activity of the zinc salt due to reactions such as chelation, and should not irritate or have other adverse effects on the genitals.

The complete gel mixture must be physiologically safe and acceptable when used repeatedly, during numerous acts of intercourse over a period of months or years, and it must not irritate mucous membranes or other genital surfaces even when rubbed in vigorously, as often occurs during intercourse. The gel must also be free of anti-coagulants (particularly heparin or dextran sulfate) or other components which could pose a risk of adverse effects in a significant portion of the population.

Apparent Ability of zinc to Inhibit HIV

In addition to reducing the risk of infection by herpes viruses, zinc salts used in genital lubricants may also be able to reduce the risk of infection by the human immunodeficiency virus (HIV). Examples 8–10, below, provide data indicating that in a two-step incubation assay involving a first incubation of zinc acetate with HIV viruses, before susceptible lymphocyte cells are added for the second incubation step, the zinc inhibited or entirely inactivated the HIV particles.

This two-step incubation assay grew out of the realization by the Applicant that, while zinc is toxic to lymphocytes (white blood cells) at the concentrations of interest, such concentrations will never be reached or even approached in the bloodstream, regardless of the concentration of zinc in a topical genital lubricant. As described in Vallee and Falchuk 1993, a review article which discusses the numerous physiological roles of zinc inside the body, the concentrations of zinc in the bloodstream and other bodily fluids are very tightly regulated, since zinc is a crucial cofactor for literally hundreds of enzymes and proteins. If zinc concentration in the blood starts to rise above normal levels, the body responds by using zinc-binding proteins in the blood to bind to the free zinc, thereby sequestering it in inactive form, and by inducing various secretions in the kidneys and pancreas which cause excess zinc to be excreted in the urine and feces.

In view of these factors, it became clear to the Applicant that the standard screening assays used by the National Cancer Institute and others (such as the assays described in Weislow et al 1989) cannot provide an adequate screening test to evaluate potential anti-viral agents that might be safe and effective in topical genital lubricants. The standard assays involve mixing together HIV particles, a candidate anti-viral drug, and susceptible lymphocytes, and culturing all three components together in a single long incubation period. Those assays cannot model or simulate what happens inside a vagina during and after intercourse, where an anti-viral drug might be able to inactivate HIV particles before the viruses can penetrate through the skin, enter the bloodstream, and contact susceptible lymphocytes. If an anti-viral drug in a topical lubricant can inactivate HIV particles inside the vagina, before the HIV particles can reach the bloodstream, and if the drug will not penetrate the mucous membranes and enter the blood at dangerous levels, then the drug might be safe and effective as a topical genital lubricant regardless of how toxic it may be to lymphocytes.

To evaluate this possibility, the Applicant developed and tested a two-step incubation assay, as mentioned above and as described in more detail in Examples 8 and 9. The first step of this assay models what happens inside the vaginal cavity. The candidate anti-viral drug (zinc acetate) was mixed and incubated for a relatively brief period (two hours, in the tests used by the Applicant) with HIV particles. Following this first incubation step, the zinc/virus mixture was diluted to a concentration where (1) the zinc would not be toxic to lymphocytes, but (2) the viral particles would still have sufficiently high concentrations to be highly infective. Susceptible lymphocyte cells were then added to this mixture, and a second incubation step was carried out for 20 days or longer, to determine whether zinc-treated or untreated HIV viruses would infect the lymphocytes.

The results, shown in FIGS. 1–4, clearly indicate that the zinc pretreatment step either (1) totally inactivated the HIV viruses, in tests involving high-concentration zinc acetate or diluted viruses, or (2) inhibited, suppressed, and delayed the infectivity of the HIV particles, in other tests involving extraordinarily high concentrations of HIV that will not occur in nature.

In addition to these data, the Applicant has discovered that it may be a valuable trait for zinc salts in a genital lubricant to be toxic to lymphocytes. It has been reported that epithelial cells (which cover the surfaces of mucous membranes) can be infected by HIV, even though epithelial cells do not have the CD4 receptor proteins that HIV particles normally bind to. This infection occurs by means of a cell-cell binding reaction which bypasses the normal virus-cell binding mechanism. In the cell-cell binding reaction, HIV-infected lymphocytes in an ejaculate from an HIV-infected male apparently can bind to epithelial cells on the surfaces of mucous membranes. The HIV-infected lymphocytes then inject HIV particles directly into the epithelial cells (Levy 1988; Phillips and Bourinbaiar 1992; Pearce-Pratt and Phillips 1993; Zacharopoulos et al 1992). Therefore, if a genital lubricant contains a zinc salt at a concentration which is toxic to lymphocytes, then the zinc salt will reduce or eliminate the ability of HIV-infected lymphocytes in an ejaculate to carry out the cell-cell infection mechanism. This appears to be a highly useful property of zinc-containing genital lubricants which is completely independent of the direct action of zinc ions in inhibiting free-floating virus particles.

It should also be noted that semen and ejaculates contain extraordinarily high concentrations of zinc. While zinc is present in blood at tightly regulated concentrations of only about 1 μg/ml, zinc is present in semen at up to 500 μg/g, and in prostate fluid at up to 1000 μg/g (Eliasson and Lindholmer 1971; Fair et al 1976; Homonnai et al 1978; Marmar et al 1980). In prostate fluid, zinc exerts an antimicrobial effects, to combat infections that cannot be directly combatted by the immune system (Fair et al 1976). And in undiluted semen, zinc suppresses the respiratory activity and motility of sperm cells (Eliasson 1971; Paz et al 1977). Apparently, this allows the sperm cells to stay in a quiescent state, storing and conserving their energy until it is needed. After ejaculation, the zinc is diluted by the female's vaginal fluids and by binding to proteins and cell surfaces inside the vagina. This decrease in the concentration of sperm-bound zinc after ejaculation allows the respiratory activity and motility of the sperm to increase.

Finally, it should also be noted that there is a very rapid turnover of epithelial cells on the surfaces of mucous membranes inside the vagina. After an epithelial cell reaches the surface of a membrane inside the vagina, it usually remains there only about four days before it is sloughed off and washed out of the vagina by the normal flow of vaginal fluids (Averette et al 1970; Ferenczy et al 1979).

The foregoing physiological factors are important, because they indicate that the mucous membranes in the vagina are adapted to withstanding concentrations of zinc that may be hundreds of times higher than lymphocytes can withstand.

EXAMPLES

EXAMPLE 1

GENITAL IRRITATION TESTS USING ZINC ACETATE

In all examples, the test subjects were a monogamous married couple, free of genital herpes or any other sexually transmitted viruses.

Zinc acetate was purchased from Pfaltz and Bauer (Waterbury, Conn.). About 0.5 grams were mixed with several drops of distilled water at room temperature. Upon stirring, the salt dissolved completely. The aqueous mixture was rubbed into an area about 3 cm in diameter on the forearm of the male and caused no irritation. Subsequently, about 0.5 grams of the salt were dissolved in a few drops of distilled water, then 10 ml K-Y Lubricating Jelly (sold by Johnson and Johnson, New Brunswick, N.J.) was added to form a gel mixture containing about 5% zinc acetate (w/v). This commercially available mixture contains purified water, hydroxyethyl-cellulose as a thickening agent, glycerin as a lubricant, glucono-delta-lactate to prevent crystallization, chlorhexidine gluconate as a preservative, and sodium hydroxide to reduce the acidity.

The mixture of zinc acetate in K-Y Lubricating Jelly was tested on the male genitals, passively at first and then with active rubbing. It caused no irritation in either test.

When 0.5 grams of zinc acetate was dissolved in distilled water and applied to the shallow region of the vagina by the female volunteer, it caused an unpleasant tingling or mild burning sensation that subsided within about ten seconds. However, when mixed with K-Y Lubricating Jelly (5% w/v as above) and applied to the shallow region of the vagina in a gel mixture, it caused no tingling, burning, or other unpleasant sensation in a passive test.

Subsequently, the gel formulation was applied topically and used as a sexual lubricant during intercourse. Both people wiped off the excess with a tissue after intercourse, but neither person showered or washed off the lubricant until the following day. It caused no irritation to either person.

EXAMPLE 2

ZINC PROPIONATE

Zinc propionate was purchased from Pfaltz and Bauer. About 0.5 grams were dissolved in several drops of distilled water and tested on the male's forearm and genitals. Although no irritation occurred on the skin in either location, the aqueous mixture caused substantial irritation to the urethra.

About 10 ml of K-Y Lubricating Jelly was added to the aqueous mixture, to create a gel mixture of about 5% w/v, which was tested, passively at first and then with active rubbing, on the male's genitals. It did not cause any irritation in either test. Another quantity of a 5% w/v gel mixture was prepared and tested passively in the shallow regions of the female's vagina. It caused no irritation, so it was used as a lubricant during intercourse. Both people wiped off the excess with a tissue after intercourse, but neither person showered or washed off the lubricant until the following day. It caused no irritation to either person.

EXAMPLE 3

ZINC GLUCONATE

Zinc gluconate was purchased from Ruger Chemical Company (Irvington, N.J.). It came in the form of a white granular powder which was gritty and interspersed with hard granules of varying sizes. About 0.5 grams were ground into a fine powder using a mortar and pestle for several minutes. The grinding was repeated after several drops of distilled water were added, and again after 10 ml of K-Y Lubricating Jelly was added. The concentration of the zinc gluconate in the gel mixture was about 5% w/v.

The mixture of zinc gluconate and K-Y Lubricating Jelly was tested on the forearm, male genitals, and female genitals. It caused no irritation, so it was applied and used as a lubricant during intercourse. Although it caused no irritation and no abrasion was noticeable by either person during intercourse, the finely ground particles in the gel displayed a very slight roughness when rubbed hard between the forefinger and thumb. Therefore, unless zinc gluconate can be thoroughly dissolved in a gel by means such as heating or addition of an additional agent to increase solubility, zinc gluconate is not preferred, because of the potential for microabrasions by any undissolved particles that remain suspended in the gel without fully dissolving.

EXAMPLE 4

ZINC STEARATE, SALICYLATE, AND VALERATE

Zinc stearate, zinc salicylate, and zinc valerate were purchased from Pfaltz and Bauer. All three salts were tested for irritation on the forearm and male genitals, and none caused any irritation. However, due to other drawbacks, they were not tested during intercourse. Zinc stearate and zinc salicylate are insoluble in water, even when mixed with hot water and ground for several minutes using a mortar and pestle. In addition, both have strong unpleasant odors. Zinc valerate, although soluble in water, has an unappealing dirty-looking color and a strong unpleasant odor.

EXAMPLE 5

ZINC SULFATE

Zinc sulfate in crystalline form was purchased from Sigma Chemical Company (St. Louis, Miss.). One gram was ground into a fine powder in a mortar and pestle, then 15 ml of K-Y Lubricating Jelly was added and thoroughly mixed. The mixture did not cause any irritation to the male's forearm, genital skin, or urethra, even when rubbed in actively. However, it caused a tingling, burning sensation when applied in a passive test to the female, so it was not tested during intercourse.

EXAMPLE 6

ZINC CHLORIDE

Zinc chloride in crystalline form was purchased from Sigma Chemical Company (St. Louis, Miss.). One gram was ground into a fine powder using a mortar and pestle, then dissolved in water and applied to the forearm of the male. It caused a burning sensation and was not tested further.

EXAMPLE 7

ZINC OXIDE

Zinc oxide, which is not a salt in the normal chemical sense, is known to cause little or no irritation. For example, an ointment sold under the trade name "Desitin" (Pfizer, Inc., New York City), which contains 40% zinc oxide, is spread on baby bottoms to control diaper rash and other skin irritations. Other zinc oxide ointments are also applied to the skin for various purposes, such as on the nose to prevent sunburn. One such ointment, sold at Walgreen's (Walgreen Laboratories, Chicago, Ill.), contains 20% zinc oxide in an ointment base of white wax, petrolatum, and mineral oil.

In skin irritation tests using the Walgreen's 20% ointment, tests on the forearm or male genitals were deemed unnecessary. Approximately 5 ml of the 20% zinc oxide ointment was mixed with K-Y Lubricating Jelly to reduce the viscosity of the zinc ointment. The mixture was tested passively by the woman to ensure that it did not cause any irritation, then it was used as a lubricant during intercourse. Other than being a bit sticky and viscous, it did not cause any significant irritation to either person.

While the zinc acetate and propionate gels were clear, zinc oxide is a bright, opaque white color. Therefore, it is more likely to generate visible stains on bedsheets and underwear than water-soluble zinc salts.

EXAMPLE 8

HIGH-TITER HIV INFECTIVITY TESTS

HIV tests were carried out at Biotech Research Laboratories (Rockville, Md.). The HIV-1 viral isolate and H-9 cell line were originally supplied by Robert Gallo of the NCI.

In a first set of tests, 20 mg of zinc acetate powder (ZnAc, MW 183.4) was mixed in 1 ml RPMI cell culture medium (Whittaker Corp.). This 2% (w/v) salt mixture contained 7 mg/ml elemental Zn. Although ZnAc is highly soluble in water, it generated a precipitate in the culture medium, which contains protein. Therefore, a small quantity of HCl was added until the mixture became clear; the pH was about 5.5. The Zn concentration was reduced by half (and the pH was raised somewhat) when an equal volume (1 ml) of cell-free high-titer HIV-1 viral stock was added. The zinc/virus mixture was stirred and incubated for 2 hours at 37° C.

Following this first incubation step, the zinc/virus mixtures were diluted at 1:10, 1:30, and 1:100 ratios using culture medium, and aliquots were added to equal volumes of culture media containing H-9 lymphocytes that had been pretreated overnight with 2 μg/ml Polybreen. The lymphocyte mixtures were incubated for three hours at 37° C.; zinc concentrations during this step were 180, 60, and 18 μg/ml for the 1:10, 1:30, and 1:100 dilutions.

The cell aliquots were then washed twice, using culture medium, to remove free p24 proteins that are present in the initial viral stock. Such proteins will skew ELISA readings if not removed by washing. Cells were then resuspended in fresh medium containing 10% fetal calf serum (FCS) and cultured for 20 days. During this period, each tube was periodically sampled by hand-mixing the tube, withdrawing 100 μl of liquid from the top, and testing the sample for p24 antigens using ELISA assays.

The 1:10 dilutions, which contained 180 µg/ml Zn during the 3-hour incubation prior to washing, caused substantial mortality to the lymphocytes, and resulting ELISA data were discarded.

Based on visual observations, 1:30 dilutions (60 µg/ml Zn) retarded cell growth during the first few days; however, any such effect disappeared within a few days and the cells grew well during the rest of the assay period.

A positive control was used at each dilution. Viral aliquots not treated with zinc were identically diluted, mixed with lymphocytes, cultured, and tested. Negative controls were also run, in which H-9 cells were plated and grown in the absence of any virus or zinc; these provided background levels that vary slightly from day to day, depending on factors such as spectrophotometer calibrations and rinsing conditions.

Figure 1:
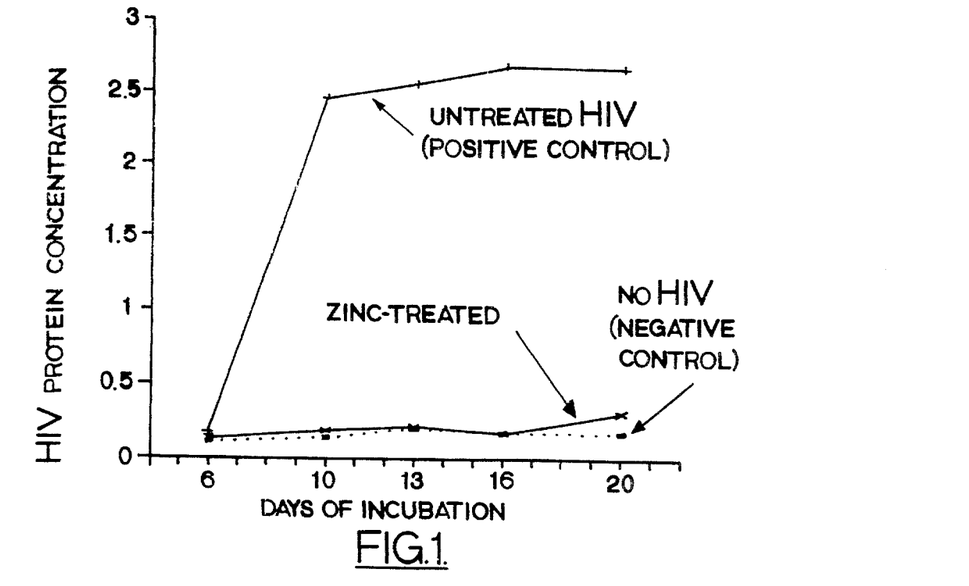
FIG. 1 shows that HIV infectivity was completely eliminated when concentrated viral stocks were incubated with 1% zinc acetate for 2 hours before the zinc-virus solution was diluted (1:30) and mixed with susceptible lymphocytes.

Optical density (OD) data from the 1:30 dilution test are shown in FIG. 1. These quantities are averages based on triplicate samples. The p24 concentrations were indistinguishable from background levels, which indicates that the zinc treatment completely abolished viral infectivity.

Figure 2:
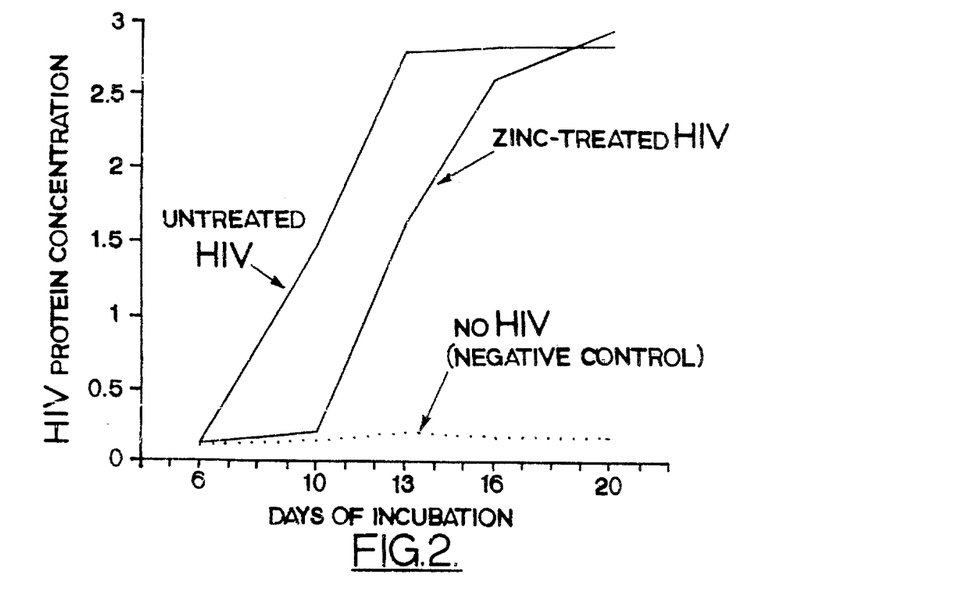
FIG. 2 shows that HIV infectivity was reduced and delayed when concentrated viral stocks were incubated with 1% zinc acetate for 2 hours before the zinc-virus solution was diluted (1:100) and mixed with lymphocytes.

Data from the 1:100 dilution test are shown in FIG. 2. One of the tubes became infected by mold after the 10th day, so subsequent values are based on averages from two samples. These results indicated that the zinc suppressed and retarded HIV infectivity; however, apparently, some small fraction of the viruses apparently remained infective.

EXAMPLE 9

DILUTED HIV INFECTIVITY TESTS

The tests described above, in Example 8, used an undiluted high-titer viral stock, which contained at least ten million infectious viral particles per ml. That concentration can be achieved in a laboratory only by special culturing, purification, and concentration techniques, and it is vastly higher than would actually occur in the ejaculate of an HIV-infected person (especially someone who is not in the end stages of the disease, and who might pose a significant risk of transmitting the virus to an uninfected and unknowing sexual partner).

In a subsequent series of tests, ZnAc was tested against diluted viral stocks; in these tests, the zinc completely eliminated the infectivity of the infected viruses. These tests used serial dilutions of the viral stocks, at ranges from 1:10 to 1:10,000. To create the 1:10 dilution, 500 µl of viral stock was mixed with 4.5 ml of RPMI medium. Subsequent dilutions added 9 ml of RPMI medium to 1 ml from the preceding dilution.

A 2 ml aliquot from each dilution was mixed with an equal volume of 3% ZnAc dissolved in sterile distilled water; after mixing, the zinc concentration was 5.3 mg/ml Zn. These mixtures were incubated for 2 hours, then diluted with culture medium at 1:30, 1:100, and 1:1000 to reduce the toxicity of the zinc to lymphocytes. Four ml of lymphocytes were mixed with 4 ml of each zinc/virus mixture. The zinc/virus/cell mixtures were incubated at 37° C. for 3 hours; zinc concentrations were 88, 27, and 2.7 µg/ml in the 30, 100, and 1000 dilutions. During subsequent culturing, significant cell mortality was observed in the 88 µg/ml treatment batch, but no cell mortality was observed at the lower levels.

Following the 3 hour incubation, the cells were washed twice in RPMI medium and resuspended in fresh medium containing 10% FCS. Each solution was inoculated (2 ml; estimated minimum $2 \times 10^5$ cells per well) into each of three wells in a 12-well plate and cultured for 27 days, with periodic sampling and measuring of p24 antigens.

Figure 3:
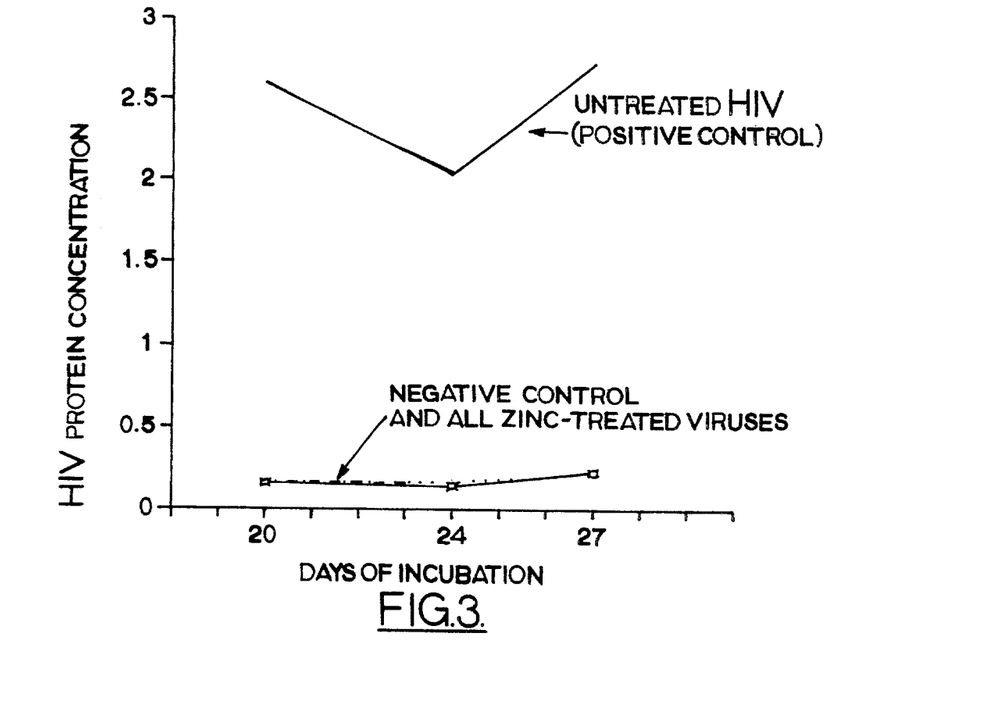
FIG. 3 shows that HIV infectivity was completely eliminated when various dilutions of high-titer viral stocks were incubated with 1.5% zinc acetate for 2 hours.

ELISA data for the 10x, 100x, and 1000x high-titer viral stock dilutions, treated with the 1000x dilution of the zinc/virus mixture (2.7 µg/ml Zn final concentration) are shown in FIG. 3. As shown, the zinc treatment completely blocked infectivity. Data for the diluted viral stocks treated with 1:100 zinc/virus dilutions (27 µg/ml Zn) were virtually identical, and viral infectivity was completely blocked.

Negative controls were identically diluted cells that did not contain zinc or HIV. Positive controls used 1:1000 dilutions of viral stock mixed with zinc-free RPMI. These controls were consistently highly infectious, even though their concentrations were 100x lower than the 1:10 mixtures in which infectivity was eliminated by zinc treatment. Other positive controls were tested at up to 100,000x dilutions; these were highly infective in two out of the three plates tested.

Figure 4:
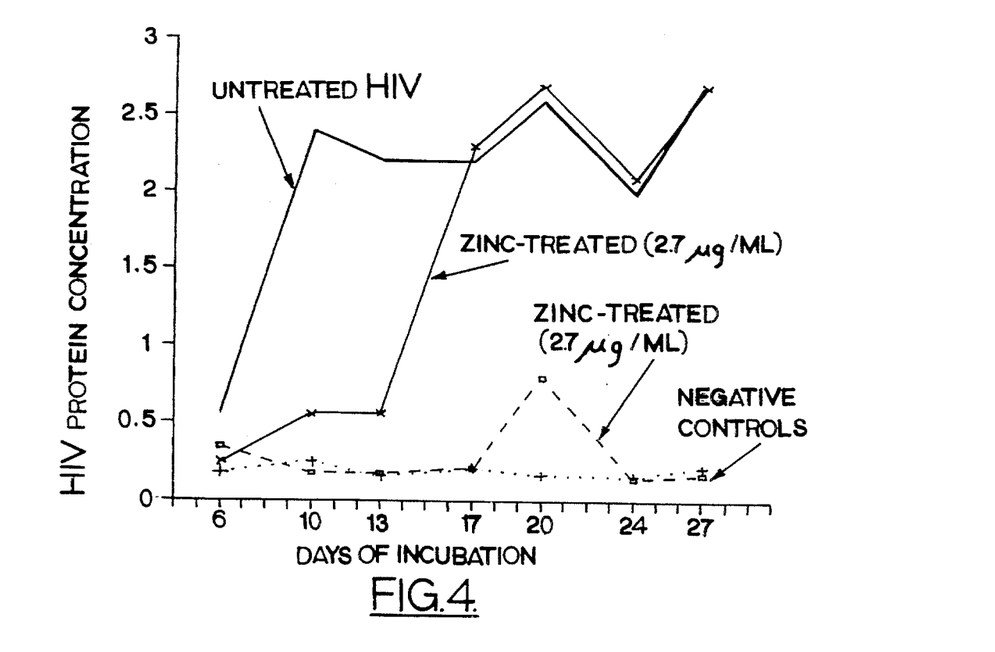
FIG. 4 shows that HIV infectivity was either eliminated or suppressed when high-titer viral stocks were incubated with various concentrations of zinc acetate.

While carrying out the viral dilution tests, tests were also performed using 2 ml of 3% ZnAc solution in distilled water mixed with 2 ml aliquots of undiluted viral stock. The zinc/virus mixtures were incubated for 2 hours, diluted with RPMI at 1:100 and 1:1000 ratios, and mixed with lymphocytes for three hours; zinc concentrations were 27 and 2.7 µg/ml. The cells were washed twice, inoculated into 12 well plates as described above, and cultured for 27 days. ELISA results are shown in FIG. 4. As shown, the 1:100 dilution (27 µg/ml Zn) completely prevented infectivity, while the 1:1000 dilution (2.7 µg/ml) delayed the onset of infection.

EXAMPLE 10

HIV PRECIPITATION TESTS

Precipitation tests were also performed, using 2% ZnAc which was mixed with an equal volume of undiluted viral stock, incubated for 24 hours, and centrifuged at 1500 rpm in a tabletop centrifuge for 5 minutes. The supernatant was sampled (100 µl) and serially diluted by medium, at 1:10 followed by 2x dilutions (1:20, 1:40, 1:80, etc) to a maximum dilution of 1:10240. Each dilution was analyzed spectrophotometrically to determine the concentration of viruses suspended in solution. After sampling, each tube was hand-mixed and incubated for 24 hours. The solution near the top of the tube was sampled again, serially diluted, and tested using the ELISA assay. The tube was hand-mixed again, incubated for three more days, and sampled again to obtain Day 5 values.

The values for zinc-treated viruses averaged about 40% less than values for identically diluted solutions that did not receive zinc treatment. This indicates that the zinc caused substantial precipitation of the virus and lowered the concentration of free HIV particles in solution.

Thus, there has been shown and described a new and useful method of reducing the risk of infection by sexually transmitted viruses, in people who were not previously infected. Although this invention has been exemplified for purposes of description and illustration by reference to certain specific embodiments, it will be apparent to those skilled in the art that various modifications and alterations of the illustrated examples are possible. Any such equivalents which derive directly from the teachings herein, and which do not depart from the spirit and scope of the invention, are deemed to be covered by this invention.

REFERENCES

Aliabeva, A. P., "Use of heparin applications in a dimethyl sulfoxide medium in the overall treatment of rheumatoid arthritis in children," *Pediatriia* 9:50–1 (1980)

Averette, H. E., et al, "Autoradiographic analysis of cell proliferation kinetics in human genital tissue," *Amer. J. Obstet. Gynec.* 108: 8–17 (1970)

Brody, I., "Topical treatment of recurrent herpes simplex ... zinc sulphate solution," *Brit. J. Dermatol.* 104: 191–194 (1981)

Cannan, R. K., and Kibrick, A., "Complex formation between carboxylic acids and divalent metal cations," *J. Amer. Chem. Soc.* 60: 2314 (1938)

Chvapil, M., et al, "Reaction of vaginal tissue of rabbit and of cheek pouch of hamster to inserted collagen sponges treated with either zinc or copper," *Am. J. Obstet. Gynecol.* 130: 63–70 (1978)

Chvapil, M., et al, "Preliminary testing of the contraceptive collagen sponge," *Obstet. and Gynecol.* 56: 503–506 (1980)

Cooper, H. S., et al, "Clinicopathologic study of dextran sulfate sodium experimental murine colitis," *Laboratory Investigations* 69: 238–249 (1993)

DeRoeth, A., "Treatment of herpetic keratitis," *Am. J. Ophthalmol.* 56: 729–731 (1963)

Eby, G. A., and W. W. Halcomb, "Use of topical zinc to prevent recurrent herpes simplex infection: review of literature and su yggested protocols," *Medical Hypotheses* 17: 157–165 (1985)

Eliasson, R. and Lindholmer, C., "Zinc in human seminal plasma," *Andrology* 3: 147 (1971)

Eliasson, R., "Effect of zinc on human sperm respiration," *Life Science* 10: 1317 (1971)

Fahim, M., et al, "New treatment for herpes simplex virus type 2: Male patients," *J. Medicine* 9 (3): 245–264 (1978)

Fahim, M., et al, "New treatment for herpes simplex virus type 2: Female patients," *J. Medicine* 11(2&3):143–167 (1980)

Fahim, M. S. and Brawner, T. A., "Treatment of genital herpes simplex virus in male patients," *Arch. Andrology* 4: 79–85 (1980)

Fair, W. R., et al, "Prostatic antibacterial factor, identity and significance," *Urology* 7: 169–177 (1976)

Ferenczy, A. and Guralnick, M. S., "Morphology of the human vagina," pp. 3–12 in *Biology of the Fluids of the Female Genital Tract*, ed. by F. K. Beller and G. F. B. Schumacher (Elsevier, N.Y., 1979)

Fridlender, B., et al, "Selective inhibition of herpes simplex virus type 1 DNA polymerase by zinc ions," *Virology* 84: 551–554 (1978)

Gordon, Y. J., et al, "Irreversible inhibition of herpes simplex virus replication in BSC-1 cells by zinc ions," *Antimicrob. Agents Chemother.* 8: 377–380 (1975)

Griessar, R., et al, *Inorg. Nuclear Chem. Letters* 4: 443 (1968)

Gupta, P. and Rapp, F., "Effect of zinc ions on synthesis of herpes simplex virus type 2-induced polypeptides," *Proc. Soc. Exp. Biol. and Med.* 152: 455–458 (1976)

Homonnai, Z. T., et al, "Prolactin and zinc in the human ejaculate," *Andrologia* 10: 66 (1978)

Jones, R., "Genital herpes and zinc," *Med. J. Australia*, Apr. 7, 1979, p. 286

Levy, J. A., "The transmission of AIDS: The case of the infected cell," *JAMA* 259: 3037–3038 (1988)

Lide, D. R., ed., *CRC Handbook of Chemistry and Physics*, 71st Edition (Boca Raton, Fla., 1990)

Linke, W. F., ed., *Solubility of Inorganic and Metal Organic Compounds*, 4th Edition Marmar, J. L., "Values for zinc in whole semen, fractions of split ejaculate, and expressed prostatic fluid," *Urology* 16: 478–480 (1980)

Pearce-Pratt, R. and Phillips, D. M., "Studies of adhesion of lymphocytic cells: Implications for sexual transmission of HIV," *Biol. of Reproduction* 48: 431–445 (1993)

Powis, G., et al, "Inhibition of growth factor binding and intracellular Ca2+ signalling by dextran sulfates of different sizes and degrees of sulfation," *Cancer Chemother. Pharmacol* 30: 83–486 (1992)

Shlomai, J., et al, "Effect of zinc ions on the synthesis of herpes simplex virus DNA in infected BSC-1 cells," *Virology* 66: 330–335 (1975)

Sillen, L. G., and Martell, A. E., *Stability Constants of Metal Ion Complexes*, Special Publication No. 17 (The Chemical Society, London, 1964)

Sillen, L. G., and Martell, A. E., *Stability Constants of Metal Ion Complexes*, Special Publication No. 25 (The Chemical Society, London, 1971)

Sorimachi, K., et al, "Inhibition of fibroblast growth by polyanions; effects of dextran sulfate and lignin derivatives," *Cell Biol. Internatl. Reports* 16: 63–71 (1992)

Tennican, P. O., et al, "The diverse effects of topical and systemic administration of zinc on the virulence of herpes simplex genitalis," *Life Sciences* 24: 1877–1884 (1979)

Tennican, P., et al, "Topical zinc in the treatment of mice infected intravaginally with herpes genitalis virus," *Proc. Soc. Exp. Biol. Med.* 164: 593–597 (1980)

Vallee, B. I. and Falchuk, K. H., "The biochemical basis of zinc physiology," *Physiological Reviews* 73: 79–118 (1993)

Van Osselaer, N., et al, "Dextran sulphate inhibits neutrophil emigration and neutrophil-dependent plasma leakage in rabbit skin," *Agents & Actions* 38: C51–53 (1993)

Wahba, A., "Topical application of zinc solutions: A new treatment for herpes simplex infections of the skin?" *Acta Derm. Venerol. (Stockholm)* 60: 175–177 (1980)

White, P. W., et al, "Thrombotic complications of heparin therapy, including six cases of heparin-induced skin necrosis," *Annals of Surgery* 190: 595–608 (1979)

Williams, W. L., "New antifertility agents active in the rabbit vaginal contraception method," *Contraception* 22:659–672 (1980)

Wright, T. C., et al, "Inhibition of rat cervical epithelial cell growth by heparin and its reversal by epidermal growth factor," *J. Cellular Physiology* 125: 499–506 (1985)

Wright, T. C., et al, "Metabolic effects of heparin on rat cervical epithelial cells," *J. Cellular Physiology* 127: 255–262 (1987)

Yamada, M. et al, "Occurrence of dysplasia and adenocarcinoma after experimental chronic ulcerative colitis in hamsters induced by dextran sulphate sodium," *Gut* 33: 1521–27 (1992)

I claim:

1. A method of reducing the risk of infection by at least one sexually transmitted virus selected from the group consisting of genital herpes viruses and human immunodeficiency viruses, comprising the step of spreading a lubricant gel upon genital surfaces of a person previously uninfected by the sexually transmitted virus, in a manner which causes the lubricant gel to coat and remain in contact with the genital surfaces during sexual intercourse, wherein:

a. the lubricant gel comprises (1) water, (2) a thickening agent, (3) a lubricating agent which reduces genital friction during sexual intercourse, and (4) a selected water-soluble organic zinc salt at a concentration of about 0.5% to about 30% measured as weight per volume;

b. the selected zinc salt, when dissolved in water, ionically dissociates at a rate sufficient to release divalent zinc ions at a concentration which significantly inhibits genital herpes viruses;

c. the lubricant gel is physiologically acceptable, does not irritate any genital surfaces when used as a topical lubricant during intercourse, and is characterized by the absence of any anti-coagulant compound or other component at a concentration that would generate a significant adverse effect upon genital surfaces if the lubricant gel is used repeatedly as a genital lubricant over a period of months.

2. The method of claim 1 wherein the zinc salt is selected from the group consisting of zinc acetate, zinc propionate, zinc butyrate, zinc formate, zinc gluconate, zinc glycerate, zinc glycolate, and zinc lactate.

3. The method of claim 1 wherein the thickening agent is selected from the group consisting of cellulose and chemically treated derivatives of cellulose, acacia, agar, alginate, carrageenan, gum tragacanth, xanthan gum, collagen, carboxypolymethylene, glyceryl monostearate, polyvinylpyrrolidone, and polyacrylamide.

4. The method of claim 1 wherein the lubricating agent is selected from the group consisting of glycerin, propylene glycol, polyethylene glycol, polypropylene glycol, polyisobutene, polyoxyethylene, behenic acid, behenyl alcohol, sorbitol, and polydimethylsiloxane.

5. The method of claim 1 wherein the lubricant is packaged with a condom and wherein the lubricant is spread on genital surfaces when the condom is placed in position.

6. A method of enhancing the effectiveness of a condom for reducing the risk of infection by sexually transmitted viruses, comprising the step of emplacing a lubricant-coated watertight condom device over a genital surface prior to intercourse, in a manner which causes the lubricant-coated condom device to remain in position during intercourse, wherein at least one surface of the condom is coated with a zinc-containing lubricant fluid comprising a physiologically-acceptable water-soluble carrier substance containing (a) a lubricating agent, and (b) a selected water-soluble organic zinc salt at a concentration of about 0.5% to about 30% measured as weight per volume, wherein the zinc-containing lubricant fluid does not irritate genital surfaces when used as a condom lubricant during intercourse, and wherein the lubricant fluid is characterized by the absence of any anti-coagulant compound or other component at a concentration that would generate a significant adverse effect upon genital surfaces if applied and used repeatedly as a genital lubricant over a period of months.

7. The method of claim 6 wherein the zinc salt is selected from the group consisting of zinc acetate, zinc propionate, zinc butyrate, zinc formate, zinc gluconate, zinc glycerate, zinc glycolate, and zinc lactate.

* * * * *